US00PP13948P29

(12) United States Plant Patent
Fick

(10) Patent No.: US PP13,948 P2
(45) Date of Patent: Jul. 8, 2003

(54) MONOPSIS PLANT NAMED 'ROYAL FLUSH'

(75) Inventor: Amanda Fick, George East (ZA)

(73) Assignee: Outeniqua Protea Nursery, Emerald (AU)

( * ) Notice: Subject to any disclaimer, the term of this patent is extended or adjusted under 35 U.S.C. 154(b) by 0 days.

(21) Appl. No.: 10/142,842

(22) Filed: May 10, 2002

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database 2002/05, GTI Jouve Retrieval Software, Citation for 'Royal Flush'.*

* cited by examiner

*Primary Examiner*—Bruce R. Campell
*Assistant Examiner*—Annette H. Para
(74) *Attorney, Agent, or Firm*—C. A. Whealy

(57) ABSTRACT

A distinct cultivar of Monopsis plant named 'Royal Flush', characterized by its low grounding, trailing and mounded plant habit; freely branching, dense and bushy plant form; freely flowering habit; and violet blue-colored flowers.

1 Drawing Sheet

BOTANICAL CLASSIFICATION/CULTIVAR DESIGNATION

*Monopsis unidentata* cultivar Royal Flush.

BACKGROUND OF THE INVENTION

The present Invention relates to a new and distinct cultivar of Monopsis plant, botanically known as *Monopsis unidentata*, and hereinafter referred to by the name 'Royal Flush'.

The new Monopsis is a product of a planned breeding program conducted by the Inventor in George, South Africa. The new Monopsis originated from a cross-pollination made by the Inventor of two unidentified proprietary *Monopsis unidentata* selections, not patented. The new Monopsis was selected by the Inventor in March, 1998 as a single plant within the progeny of the cross-pollination on the basis of its freely flowering habit and violet blue-colored flowers.

Asexual reproduction of the new cultivar by terminal cuttings taken at George, South Africa, since April, 1998, has shown that the unique features of this new Monopsis are stable and reproduced true to type in successive generations.

SUMMARY OF THE INVENTION

Plants of the cultivar Royal Flush have not been observed under all possible environmental conditions. The phenotype may vary somewhat with variations in environment such as temperature and light intensity without, however, any variance in genotype.

The following traits have been repeatedly observed and are determined to be the unique characteristics of 'Royal Flush'. These characteristics in combination distinguish 'Royal Flush' as a new and distinct Monopsis cultivar:

1. Low grounding, trailing and mounded plant habit.
2. Freely branching, dense and bushy plant form.
3. Freely flowering habit.
4. Violet blue-colored flowers.

Plants of the cultivar Royal Flush differ from plants of the parent selections primarily in plant habit and flower color.

Plants of the new Monopsis can be compared to plants of the Monopsis cultivar Lutea, not patented. In side-by-side comparisons conducted in George, South Africa, plants of the new Monopsis differed from plants of the cultivar Lutea in the following characteristics:

1. Plants of the new Monopsis were more compact and more mounded than plants of the cultivar Lutea.
2. Plants of the new Monopsis had larger flowers than plants of the cultivar Lutea.
3. Plants of the new Monopsis had violet blue-colored flowers whereas plants of the cultivar Lutea have yellow-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Monopsis.

The photograph at the top of the sheet comprises a side perspective view of three typical flowering plants of 'Royal Flush' grown in a 20-cm container for about eight weeks.

The photograph at the bottom of the sheet comprises a close-up view of typical flowers, flower buds and leaves of 'Royal Flush'.

DETAILED BOTANICAL DESCRIPTION

The aforementioned photographs and following observations and measurements describe plants grown in Bonsall, Calif., under commercial practice during the spring an open field with day temperatures ranging from 18 to 35° C. and night temperatures ranging from 7 to 18° C. Three rooted young plants were planted in 20-cm containers and grown for about eight weeks. In the following description, color references are made to The Royal Horticultural Society Colour Chart, 1995 Edition, except where general terms of ordinary dictionary significance are used.

Botanical classification: *Monopsis unidentata* cultivar Royal Flush.

Parentage:

*Female parent.*—Unidentified proprietary *Monopsis unidentata* selection, not patented.

*Male parent.*—Unidentified proprietary *Monopsis unidentata* selection, not patented.

Propagation:

*Type cutting.*—Terminal vegetative cuttings.

*Time to initiate roots.*—About 21 days at 20° C.

*Time to produce a rooted young plant.*—About 35 to 38 days at 21 to 24° C.

*Root description.*—Fibrous; white in color.

Plant description:

*Form.*—Low growing, trailing and mounding flowering plants with violet blue-colored flowers. Very freely branching with lateral branches potentially forming at every node; dense and bushy plants. Moderately vigorous growth habit.

*Plant height.*—About 12 cm.

*Plant diameter*—About 22 cm.

*Lateral branch description.*—Length: About 25 cm. Diameter: About 1.5 mm. Internode length: About 1.5 cm. Texture: Smooth, glabrous. Color: 144A.

*Foliage description.*—Arrangement: Simple; before flowering, opposite; after flowering, alternate. Length: About 2.6 cm. Width: About 6 mm. Shape: Lanceolate with about three small lobes. Apex: Acute. Base: Attenuate. Margin: Entire with about three small lobes. Texture, upper and lower surfaces: Smooth, glabrous. Venation pattern: Pinnate. Petiole length: About 2 mm. Petiole diameter: About 1 mm. Color: Young and fully expanded foliage, upper surface: 146A. Young and fully expanded foliage, lower surface: 146B. Venation, upper and lower surfaces: 146B. Petiole: 144A.

Flower description:

*Flower type and habit.*—Single axillary flowers with three banner petals and two lower petals; zygomorphic. Flowers initially upright then held outwardly. Freely and continuously flowering, about two or three open flowers and about 20 flower buds per lateral branch. Flowers not fragrant. Flowers persistent.

*Natural flowering season.*—May through October in Bonsall, Calif.

*Flower longevity on the plant.*—Typically five to seven days.

*Flower size.*—Length: About 1.2 cm. Diameter: About 1.5 cm. Depth (height): About 1.4 cm.

*Flower buds.*—Length: About 1.2 cm. Diameter: About 3 mm. Shape: Obovate. Color: 147D.

*Petals.*—Arrangement: Single whorl of five petals, fused at base; three banner petals and two lower petals. Length, banner petals: About 1.3 cm. Length, lower petals: About 1.1 cm. Width, banner petals: About 4 mm. Width, lower petals: About 5 mm. Shape, all petals: Elliptic. Apex, all petals: Acute. Base, all petals: Fused. Margin, all petals: Entire. Texture, all petals, upper and lower surfaces: Smooth, velvety. Color, all petals: When opening, upper surface: 90A. When opening, lower surface: 90C. Fully opened, upper surface: 90C, color fading to 85A to 85B with subsequent development; towards the base of banner petals, 79A, color fading to 83A to 83B with subsequent development. Fully opened, lower surface: 85D.

*Sepals.*—Arrangement: Single whorl of five sepals fused at base, star-shaped. Length: About 5 mm. Width: About 1 mm. Shape: Lanceolate. Apex: Acute. Margin: Entire. Texture, upper and lower surfaces: Smooth, glabrous. Color, upper surface: 147A. Color, lower surface: 147B.

*Peduncle.*—Strength: Flexible and wiry. Length: About 5.5 cm. Diameter: Less than 1 mm. Angle: About 45 to 60° from vertical. Color: 144A.

*Reproductive organs.*—Stamens: Quantity/arrangement: Five; filaments free, anthers fused around style. Anther length: About 3 mm. Anther shape: Oblong. Anther color: 177A. Pollen amount: Scarce. Pollen color: 1D. Pistils: Quantity: One. Pistil length: About 1.4 cm. Stigma shape: Bi-parted. Stigma color: 144C. Style length: About 9 mm. Style color: 144C. Ovary color: 144A.

*Seed/fruit.*—Seed and fruit production has not been observed.

Disease/pest resistence: Plants of the new Monopsis have not been noted to be resistant to pathogens or pests common to Monopsis.

Weather tolerance: Plants of the new Monopsis have exhibited good tolerance to rain and wind.

Temperature tolerance: Plants of the new Monopsis have been observed to tolerate temperatures from 0 to higher than 38° C.

It is claimed:

1. A new and distinct cultivar of Monopsis plant named 'Royal Flush', as illustrated and described.

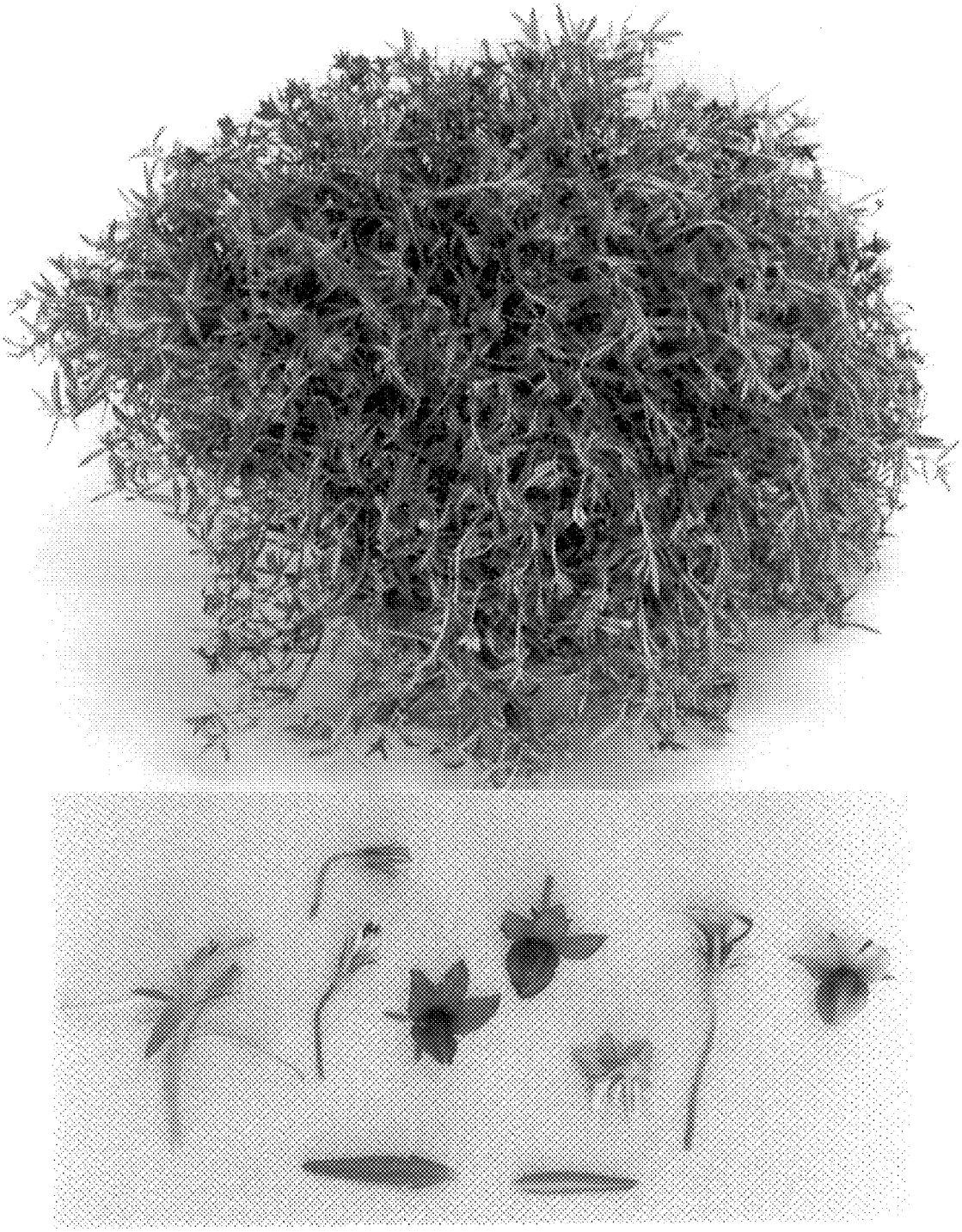

* * * * *